United States Patent [19]

Holt et al.

[11] 4,189,587
[45] Feb. 19, 1980

[54] 1,3-DIAMINOMETHYL-HYDANTOIN ADDITIVES FOR LUBRICATING OILS

[75] Inventors: Brian Holt, Stretford; Peter I. Lee, Prestwood, Nr. Great Missenden, both of England

[73] Assignee: Ciba-Geigy Corporation, Ardsley, N.Y.

[21] Appl. No.: 892,712

[22] Filed: Apr. 3, 1978

[30] Foreign Application Priority Data

Apr. 5, 1977 [GB] United Kingdom ............... 14344/77

[51] Int. Cl.$^2$ .................. C07D 233/72; C07D 235/26; C10M 1/32; C10M 1/38

[52] U.S. Cl. ..................................... 548/312; 252/47; 252/47.5; 252/49.9; 252/51.5 A; 544/82; 544/139; 544/357; 544/370; 548/308; 548/309; 548/314; 546/15; 546/187; 546/210

[58] Field of Search ............... 548/308, 309, 312, 314; 260/293.55, 268 H; 544/139

[56] References Cited

U.S. PATENT DOCUMENTS

| | | | |
|---|---|---|---|
| 2,143,816 | 1/1939 | Jacobson | 548/308 |
| 2,732,380 | 1/1956 | Reppe et al. | 548/308 |
| 3,651,062 | 3/1972 | Fatzer et al. | 548/312 X |
| 3,835,151 | 9/1974 | Havera et al. | 548/312 |
| 4,073,927 | 2/1978 | Freilich | 548/312 X |
| 4,093,809 | 6/1978 | Hall et al. | 548/308 |

FOREIGN PATENT DOCUMENTS

| | | | |
|---|---|---|---|
| 1940709 | 11/1970 | Fed. Rep. of Germany | 548/308 |
| 966395 | 10/1950 | France | 548/308 |
| 38-24380 | 11/1963 | Japan | 548/312 |
| 338465 | 7/1959 | Switzerland | 548/308 |
| 512629 | 9/1939 | United Kingdom | 548/308 |
| 667122 | 2/1952 | United Kingdom | 548/308 |
| 817745 | 8/1959 | United Kingdom | 548/312 |

OTHER PUBLICATIONS

Kawahara, Index Chemicus 1, No. 1, p. 63 (1962).
Dymek, Dissertations Pharmaceutical et Pharmacological, 1968, vol. 20, No. 5, pp. 507–524.
Orazi et al.; Tetrahedron 15, 93 (1961).
Zubenko, Farm. Zh. (Kiev), 24, (2), 18 (1969).

*Primary Examiner*—Thomas A. Waltz
*Attorney, Agent, or Firm*—Luther A. R. Hall

[57] ABSTRACT

Lubricating oil compositions, comprising as additive, from 0.001 to 10% by weight, based on the weight of the total composition, of a 1- or 3-aminomethyl-hydantoin or a 1,3-diaminomethyl-hydantoin.

6 Claims, No Drawings

1,3-DIAMINOMETHYL-HYDANTOIN ADDITIVES FOR LUBRICATING OILS

The present invention relates to lubricating compositions containing substituted hydantoins and their derivatives.

The incorporation of extreme pressure/anti-wear additives into lubricating oil basestocks, whilst preventing excessive wear, can lead to corrosion. This is particularly the case in the presence of non-ferrous metals e.g. copper.

In U.S. Patent No. 2,143,816, there are described dithiohydantoin compounds optionally substituted in the 5 position by one or two hydrocarbon radicals. These compounds are recommended for use as corrosion inhibitors for metal pickling baths, as insecticides and as resin intermediates.

We have now developed certain additives which, when incorporated into lubricating oils, inhibit corrosion caused by sulphur and phosphorus/sulphur extreme pressure and antiwear additives. The hydantoin additives of the present invention also exhibit antioxidant activity and those additives of the invention which contain sulphur also possess good extreme pressure/anti-wear activity.

According to the present invention, there is provided a lubricating oil composition containing, as additive, from 0.001% to 10%, preferably 0.1% to 5%, more preferably from 0.1% to 2% by weight, based on the weight of the total composition, of a compound of formula:

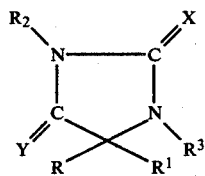
I wherein X and Y are the same or different and each is an oxygen or sulphur atom; R and $R^1$ are the same or different and each is hydrogen, a straight or branched chain alkyl group having from 1 to 18 carbon atoms, an alkenyl or alkynyl group having from 3 to 18 carbon atoms, an optionally substituted cycloalkyl group having from 3 to 12 ring carbon atoms, an optionally substituted aryl group having from 6 to 10 ring carbon atoms, an optionally substituted aralkyl group having from 6 to 10 ring carbon atoms, an optionally substituted heterocyclic residue containing from 3 to 10 ring members or R and $R^1$ together with the carbon atom to which they are attached form a mono, di-or poly-cyclic ring having from 4 to 12 carbon atoms, these rings may be saturated or unsaturated, they may also be interrupted by heteroatoms;

$R^2$ and $R^3$ are the same or different and either (a) each is hydrogen or a dihydrocarbylaminomethyl group having the formula:

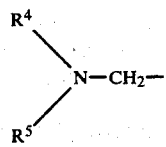

wherein $R^4$ and $R^5$ are the same or different and each is a straight or branched alkyl group having from 1 to 18 carbon atoms, an alkenyl group having from 3 to 8 carbon atoms, a cycloalkyl group having from 3 to 6 ring carbon atoms or $R^4$ and $R^5$ together with the nitrogen atom to which they are attached form a heterocyclic ring having from 4 to 7 carbon atoms, which may be interrupted by other heteroatoms, these heterocyclic rings being unsubstituted or substituted by alkyl groups having from 1 to 4 carbon atoms, alkoxy groups having from 1 to 4 carbon atoms or halogen atoms, or (b) one is hydrogen and the other is a group of formula

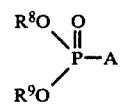

wherein A is alkylene with 2 to 12 carbon atoms and $R^8$ and $R^9$ are the same or different and each is a 1–12C alkyl or alkenyl group which may be substituted e.g. by halogen, or $R^8$ and $R^9$ together can form a 2–5 C alkylene group with the proviso that when $R^2$ and $R^3$ are each hydrogen then X and Y are both sulphur atoms.

Examples of the groups R and $R^1$ are:

| | |
|---|---|
| hydrogen | cyclopropyl |
| methyl | cyclobutyl |
| ethyl | cyclopentyl |
| n-propyl | 3-methylcyclopentyl |
| iso-propyl | cyclohexyl |
| n-butyl | 3-methylcyclohexyl |
| sec-butyl | 4-methylcyclohexyl |
| iso-butyl | cycloheptyl |
| t-butyl | cyclooctyl |
| n-pentyl | cyclodecyl |
| n-hexyl | cyclododecyl |
| iso-hexyl | phenyl |
| n-heptyl | 3-methylphenyl |
| n-octyl | 4-methylphenyl |
| t-octyl | 4-n-butylphenyl |
| iso-octyl | 4-methoxyphenyl |
| 2-ethylhexyl | 4-n-butoxyphenyl |
| n-nonyl | 3-chlorophenyl |
| n-decyl | 4-chlorophenyl |
| iso-decyl | α-naphthyl |
| n-undecyl | β-naphthyl |
| n-dodecyl | benzyl |
| n-tetradecyl | 3-methylbenzyl |
| n-hexadecyl | 4-methoxybenzyl |
| n-octadecyl | 4-chlorobenzyl |
| propenyl-1 | α-naphthylmethyl |
| 1-methylpropenyl-1 | β-naphthylmethyl |
| 3-methyl-2-butenyl-1 | 3-thienyl |
| 4-methyl-3-pentenyl-1 | 12-methyl-n-tridecenyl-1 |
| 6-methyl-5-heptenyl-1 | propynyl-1 |
| 9-methyl-8-decenyl-1 | |

Examples of the groups R and $R^1$ when, together with the carbon atom to which they are attached, they form a carboxylic ring system are:

| | |
|---|---|
| cyclohexamethylene | cyclotetramethylene |
| cycloheptamethylene | 2-methylcyclotetramethylene |
| cyclooctamethylene | cyclopentamethylene |
| cyclodecamethylene | 1-methylcyclopentamethylene |
| cyclododecamethylene | 1,2-dimethylcyclopentamethylene |

Examples of the groups R and R¹ when, together with the carbon atom to which they are attached, they form a heterocyclic ring system are:

| 3-azacyclopentamethylene | 2,2,4-trimethylcyclopentamethylene |
|---|---|
| 3-methyl-3-azacyclopentamethylene | |
| 2,2,3,4,4-pentamethyl-3-azacyclopentamethylene | |

Examples of the groups R⁴ and R⁵ are:
methyl, ethyl, n-propyl, iso-propyl, n-butyl, sect-butyl, iso-butyl, t-butyl, n-pentyl, n-hexyl, iso-hexyl, n-heptyl, n-octyl, t-octyl, iso-octyl, 2-ethylhexyl, n-nonyl, n-decyl, iso-decyl, n-undecyl, n-dodecyl, n-tetradecyl, n-hexadecyl, n-octadecyl, propenyl-1, 1-methylpropenyl-1,3-methyl-2-butenyl-1, 4-methyl-3-pentenyl-1, 7-methyl-5-heptenyl-1, cyclopropyl, cyclopentyl, 3-methylcyclopentyl, cyclohexyl, 3-methylcyclohexyl and 4-methylcyclohexyl.

Examples of the groups R⁴ and R⁵ when, together with the nitrogen atom to which they are attached, they form a heterocyclic ring are:
pyrrolidine, piperidine, 2-methylpiperidine, 3-methylpiperidine, 4-methylpiperidine, 3,5-dimethylpiperidine, morpholine, piperazine and N-methylpiperazine.

Each of R⁸ and R⁹ preferably denotes an optionally substituted alkyl or alkenyl with 1 to 4 carbon atoms, e.g. methyl, ethyl, propyl, butyl, allyl, butenyl or monochloroethyl, especially methyl or ethyl. A preferably denotes alkylene with 2 to 6 carbon atoms, especially ethylene.

The lubricating oil component of the composition of the present invention may be a mineral oil, a synthetic oil or any mixture of such oils. Mineral oils are preferred and examples of these include paraffinic hydrocarbon oils e.g. a mineral oil having a viscosity of 8.0 centistokes at 99° C.; "150 Solvent Neutral" a solvent refined neutral mineral oil having a viscosity of 5.34 centistokes at 99° C.; and "Solvent Brightstocks", a high-boiling residue from the process of refining mineral oil, and having a viscosity of 32.3 centistokes at 99° C.

Synthetic lubricating oils which may be present include simple di-, tri- and tetra- esters, complex esters and polyesters derived from carboxylic acids and hydroxy compounds. Preferred are dicarboxylic acid esters of formula:

R⁶—OOC—alkylene—COO R⁷ wherein "alkylene" denotes an alkylene residue having from 2 to 14 carbon atoms and R⁶ and R⁷ are the same or different and each is an alkyl group having from 6 to 18 carbon atoms.

Tri-esters which are of use as lubricating oil basestocks are those derived from trimethylolpropane and C6–C18 mono-carboxylic acids or mixtures thereof, whereas suitable tetra-esters include those derived from pentaerythritol and a C6–C18 monocarboxylic acid or mixtures thereof.

Complex esters suitable for use as components of the compositions of the present invention are those derived from monobasic acids, dibasic acids and polyhydric alcohols, for instance the complex ester derived from trimethylol propane, caprylic acid and sebacic acid.

Suitable polyesters are those derived from an aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

The lubricating oils may also be polyglycols, polyphenyl ethers, synthetic hydrocarbons, polysiloxanes, silicates, triaryl-phosphates or mixtures thereof.

Examples of specific compounds of formula I wherein R₂ and R₃ are each hydrogen include:
5,5-Dimethyl hydantoin
5-Methyl-5-n-butyl hydantoin
5-Methyl-5-n-hexyl hydantoin
5-Methyl-5-n-nonyl hydantoin
5-Methyl-5-n-undecylhydantoin
5,5-Diethyl hydantoin
5,5-Di-n-butyl hydantoin
5,5-Di-n-octyl hydantoin
5-Methyl-5-(4'-methyl-3'-pentenyl-1')hydantoin
5-Methyl-5-(3'-methyl-2'-butenyl-1')hydantoin
5-Methyl-5-(1'-methylpropenyl-1')hydantoin
5,5-Cyclotetramethylene hydantoin
5,5-2'-Methylcyclotetramethylene hydantoin
5,5-Cyclopentamethylene hydantoin
5,5-1'-Methylcyclopentamethylene hydantoin
5,5-1',3'-Dimethylcyclopentamethylene hydantoin
5,5-4'-Methylisopropylcyclopentamethylene hydantoin
5,5-Cycloheptamethylene hydantoin
5,5-Cycloundecamethylene hydantoin Examples of specific compounds of formula I wherein R² and/or R³ are dihydrocarbylaminomethyl include:

R=R¹=H 3-(Dimethylaminomethyl)hydantoin
3-(Di-isobutylaminomethyl)hydantoin
3-(Di-n-octylaminomethyl)hydantoin
3-(Di-n-tetradecylaminomethyl)hydantoin
3-(Diallylaminomethyl)hydantoin
3-(Dicyclohexylaminomethyl)hydantoin
3-(N-Pyrrolidinomethyl)hydantoin
3-(N-Methyl-n-butylamino)hydantoin
3-(N-Methyl-n-octadecylamino)hydantoin
1,3-Bis(diethylaminomethyl)hydantoin
1,3-Bis(di-n-butylaminomethyl)hydantoin
1,3-Bis(di-n-decylaminomethyl)hydantoin
1,3-Bis(di-n-dodecylaminomethyl)hydantoin
1,3-Bis(diallylaminomethyl)hydantoin
1,3-Bis(dicyclopentylaminomethyl)hydantoin
1,3-Bis(dicyclohexylaminomethyl)hydantoin
1,3-Bis(N-pyrrolidinomethyl)hydantoin
1,3-Bis(N-3'-methylpiperazinomethyl)hydantoin
1,3-Bis(N-methyl-n-hexylaminomethyl)hydantoin
1,3-Bis(N-methyl-isooctylaminomethyl)hydantoin
1,3-Bis(N-methyl-n-decylaminomethyl)hydantoin
1,3-Bis(N-methyl-n-dodecylaminomethyl)hydantoin

R=ALKYL, R¹=H 3-(Diethylaminomethyl)-5-isopropylhydantoin
3-(Di-n-hexylaminomethyl)-5-n-butylhydantoin
3-(Diallylaminomethyl)-5-n-hexylhydantoin
3-(Dicyclopentylaminomethyl)-5-n-decylhydantoin
3-(N-Piperidinomethyl)-5-n-dodecylhydantoin
3-(N-Methyl-ethylaminomethyl)-5-n-butylhydantoin
3-(N-Methyl-n-octylaminomethyl)-5-n-decylhydantoin
1,3-Bis(dimethylaminomethyl)-5-isopropylhydantoin
1,3-Bis(di-n-butylaminomethyl)-5-n-butylhydantoin 1,3-Bis(di-n-octylaminomethyl)-5-n-hexylhydantoin
1,3-Bis(di-n-tetradecylaminomethyl)-5-n-decylhydantoin
1,3-Bis(diallylaminomethyl)-5-n-undecylhydantoin
1,3-Bis(dicyclohexylaminomethyl)-5-isopropylhydantoin
1,3-Bis(N-piperidinomethyl)-5-n-hexylhydantoin
1,3-Bis(N-morpholinomethyl)-5-n-nonylhydantoin
1,3-Bis(N-methyl-n-propylaminomethyl)-5-isopropylhydantoin
1,3-Bis(N-methyl-iso-hexylaminomethyl)-5-n-hexylhydantoin R=ALKENYL, R¹=H
3-(Di-n-butylaminomethyl)-5-propenylhydantoin
3-(N-Morpholinomethyl)-5-oleylhydantoin
3-(N-Methyl-n-butylaminomethyl)-5-propenyl hydantoin
3-(N-Methyl-n-octylaminomethyl)-5-oleylhydantoin
1,3-Bis(diethylaminomethyl)-5-propenylhydantoin
1,3-Bis(dicyclohexylaminomethyl)-5-oleylhydantoin
1,3-Bis(N-methyl-n-decylaminomethyl)-5-propenylhydantoin
1,3-Bis(N-methyl-isodecylaminomethyl)-5-oleyl hydantion

R=CYCLOALKYL, R¹=H 3-(Di-n-propylaminomethyl)-5-cyclopentylhydantion
3-(Di-n-decylaminomethyl)-5-cyclooctylhydantoin
3-(Di-cyclohexylaminomethyl)-5-cyclododecylhydantoin
3-(N-Methyl-n-heptylaminomethyl)-5-cyclopropylhydantoin
3-(N-Methyl-n-dodecylaminomethyl)-5-cyclohexylhydantoin
3-(N-Methyl-n-octadecylaminomethyl)-5-cyclooctylhydantoin
1,3-Bis(diethylaminomethyl)-5-cyclopropylhydantoin
1,3-Bis(di-n-butylaminomethyl)-5-cyclopentylhydantoin
1,3-Bis(di-n-hexylaminomethyl)-5-cyclohexylhydantoin
1,3-Bis(N-methyl-ethylaminomethyl)-5-cyclopentyl hydantoin
1,3-Bis(N-methyl-n-pentylaminomethyl)-5-cyclohexyl hydantoin
1,3-Bis(N-methyl-n-octadecylaminomethyl)-5-cyclododecyl hydantoin

R=ARYL, R¹=H 3-(Di-isopropylaminomethyl)-5-phenylhydantoin
3-(Di-n-amylaminomethyl)-5-(4'-methylphenyl)hydantoin
3-(Di-2'-ethylhexylaminomethyl)-5-(3'-chlorophenyl)hydantoin
3-(Di-n-decylaminomethyl)-5-(2'-methoxyphenyl)hydantoin
3-(Di-cyclohexylaminomethyl)-5-α-naphthylhydantoin
3-(N-Piperidinomethyl)-5-β-naphthylhydantoin
3-(N-Methyl-isobutylaminomethyl)-5-phenylhydantoin
3-(N-Methyl-n-hexylaminomethyl)-5-(4'-methylphenyl)hydantoin
3-(N-Methyl-n-decylaminomethyl)-5-(3',5'-dichlorophenyl)hydantoin
3-(N-Methyl-n-octadecylaminomethyl)-5-(4'-methoxyphenyl)hydantoin

R=ARALKYL, R¹=H 3-(Di-sec-butylaminomethyl)-5-benzylhydantoin
3-(Di-allylaminomethyl)-5-(4'-chlorobenzyl)hydantoin
3-(Di-cyclopentylaminomethyl)-5-(α-naphthylmethyl)hydantoin
3-(N-Morpholinomethyl)-5-(β-naphthylmethyl)hydantoin
3-(N-Methyl-ethylaminomethyl)-5-benzylhydantoin
3-N-Methyl-n-butylaminomethyl)-5-(4'-chlorobenzyl)hydantoin
3-(N-Methyl-isohexylaminomethyl)-5-(4'-methylbenzyl)hydandoin
3-(N-Methyl-isodecylaminomethyl)-5-(α-naphthylmethyl)hydantoin
3-(N-Methyl-n-dodecylaminomethyl)-5-(β-naphthylmethyl)hydantoin

R=R¹=ALKYL 3-(Diethylaminomethyl)-5,5-dimethylhydantoin
3-(Diethylaminomethyl)-5-methyl-5-n-butylhydantoin
3-(Diethylaminomethyl)-5-methyl-5-n-undecylhydantoin
3-(Di-n-butylaminomethyl)-5,5-diethylhydantoin
3-(Di-n-butylaminomethyl)-5,5-di-n-butylhydantoin
3-(Di-isobutylaminomethyl)-5-methyl-5-ethylhydantoin
3-(Di-isobutylaminomethyl)-5-methyl-5-n-pentylhydantoin
3-(Di-n-pentylaminomethyl)-5-ethyl-5-n-hexylhydantoin
3-(Di-n-pentylaminomethyl)-5,5-di-n-butylhydantoin
3-(Di-n-hexylaminomethyl)-5-methyl-5-isopropylhydantoin
3-(Di-n-hexylaminomethyl)-5-methyl-5-nonyl hydantoin
3-(Di-n-heptylaminomethyl)-5,5-dimethylhydantoin
3-(Di-n-octylaminomethyl)-5-methyl-5-isopentylhydantoin
3-(Do-n-octylaminomethyl)-5-methyl-5-n-hexylhydantoin
3-(Di-isooctylaminomethyl)-5-methyl-5-n-undecylhydantoin
3-(Di-2'-ethylhexylaminomethyl)-5,5-di-n-octylhydantoin
3-(Di-n-decylaminomethyl)-5-ethyl-5-n-butylhydantoin
3-(Di-isodecylaminomethyl)-5,5-di-n-butylhydantoin
3-(Di-n-dodecylaminomethyl)-5-methyl-5-isobutylhydantoin
3-(Di-n-tetradecylaminomethyl)-5,5-dimethylhydantoin
3-(Di-n-tetradecylaminomethyl)-5-methyl-5-n-pentylhydantoin
3-(Di-n-tetradecylaminomethyl)-5,5-di-n-butylhydantoin
3-(Di-allylaminomethyl)-5,5-dimethylhydantoin
3-(Di-allylaminomethyl)-5-methyl-5-n-hexylhydantoin
3-(Di-cyclopentylaminomethyl)-5-methyl-5-ethylhydantoin
3-(Di-cyclopentylaminomethyl)-5-methyl-5-n-undecylhydantoin
3-(Di-cyclopentylaminomethyl)-5,5-di-n-butylhydantoin 3-(Di-cyclohexylaminomethyl)-5-methyl-5-isobutylhydantoin
3-(Di-cyclohexylaminomethyl)-5-methyl-5-n-nonylhydantoin
3-(N-Pyrrolidinomethyl)-5,5-diethylhydantoin
3-(N-Pyrrolidinomethyl)-5-methyl-5-n-pentylhydantoin
3-(N-Piperidinomethyl)-5-methyl-5-n-hexylhydantoin
3-(N-Piperidinomethyl)-5,5-di-n-butylhydantoin
3-(N-Morpholinomethyl)-5-methyl-5-n-butylhydantoin
3-(N-Morpholinomethyl)-5-methyl-5-undecylhydantoin
3-(N-3'-Methylpiperazoinomethyl)-5,5-dimethylhydantoin
3-(N-3'-Methylpiperazinomethyl)-5,5-di-n-octylhydantoin
3-(N-Methyl-n-propylaminomethyl)-5,5-dimethylhydantoin
3-(N-Methyl-isobutylaminomethyl)-5-methyl-5-n-butylhydantoin
3-(N-Methyl-n-octylaminomethyl)-5-methyl-5-n-nonylhydantoin
3-(N-Methyl-isodecylaminomethyl)-5-methyl-5-n-undecylhydantoin
3-(N-Methyl-n-octadecylaminomethyl)-5,5-di-n-butyl hydantoin
1,3-Bis(dimethylaminomethyl)-5,5-diethylhydantoin
1,3-Bis(dimethylaminomethyl)-5-methyl-5-n-propyl hydantoin
1,3-Bis(diethylaminomethyl)-5-methyl-5-n-butylhydantoin
1,3-Bis(diethylaminomethyl)-5-methyl-5-n-hexylhydantoin
1,3-Bis(di-n-propylaminomethyl)-5-methyl-5-n-nonylhydantoin
1,3-Bis(di-n-butylaminomethyl)-5-methyl-5-n-undecylhydantoin
1,3-Bis(di-isobutylaminomethyl)-5,5-diethylhydantoin
1,3-Bis(di-isobutylaminomethyl)-5-ethyl-5-n-butylhydantoin
1,3-Bis(di-n-pentylaminomethyl)-5,5-di-n-octylhydantoin
1,3-Bis(di-n-hexylaminomethyl)-5,5-dimethylhydantoin
1,3-Bis(di-n-hexylaminomethyl)-5-methyl-5-ethyl hydantoin
1,3-Bis(di-isohexylaminomethyl)-5-methyl-5-n-pentyl hydantoin
1,3-Bis(di-n-heptylamino methyl)-5-methyl-5-n-hexylhydantoin
1,3-Bis(di-n-octylaminomethyl)-5-methyl-5-n-octylhydantoin
1,3-Bis(di-n-octylaminomethyl)-5-methyl-5-n-undecylhydantoin
1,3-Bis(di-2¹-ethylhexylaminomethyl)-5,5-dimethylhydantoin
1,3-Bis(di-2¹-ethylhexylaminomethyl)-5,5-di-n-butylhydantoin
1,3-Bis(di-n-decylaminomethyl)-5-methyl-5-ethylhydantoin
1,3-Bis(di-n-decylaminomethyl)-5-methyl-5-n-hexyl hydantoin
1,3-Bis(di-n-dodecylaminomethyl)-5-methyl-5-n-decylhydantoin
1,3-Bis(di-n-tetradecylaminomethyl)-5,5-diethylhydantoin
1,3-Bis(di-n-tetradecylaminomethyl)-5,5-di-n-butylhydantoin
1,3-Bis(di-n-tetradecylaminomethyl)-5,5-di-n-octyl hydantoin
1,3-Bis(diallylaminomethyl)-5,5-dimethyl hydantoin
1,3-Bis(diallylaminomethyl)-5-methyl-5-n-hexyl hydantoin
1,3-Bis(diallylaminomethyl)-5-methyl-5-n-undecylhydantoin
1,3-Bis(diallylaminomethyl)-5,5-di-n-octylhydantoin
1,3-Bis(dicyclopentylaminomethyl)-5,5-dimethyl hydantoin
1,3-Bis(dicyclopentylaminomethyl)-5-methyl-5-n-butyl hydantoin
1,3-Bis(dicyclopentylaminomethyl)-5-methyl-5-undecyl hydantoin
1,3-Bis(dicyclohexylaminomethyl)-5,5-diethyl hydantoin
1,3-Bis(dicyclohexylaminomethyl)-5,5-di-n-butyl hydantoin
1,3-Bis(dicyclohexylaminomethyl)-5-methyl-5-n-nonyl hydantoin
1,3-Bis(N-pyrrolidinomethyl)-5,5-dimethylhydantoin
1,3-Bis(N-pyrrolidinomethyl)-5-methyl-5-n-octyl hydantoin
1,3-Bis(N-piperidinomethyl)-5-methyl-5-n-nonylhydantoin
1,3-Bis(N-piperidinomethyl)-5,5-di-n-butyl hydantoin
1,3-Bis(N-morpholinomethyl)-5-methyl-5-n-hexyl hydantoin
1,3-Bis(N-morpholinomethyl)-5,5-di-n-octylhydantoin
1,3-Bis(N-3'-methylpiperazinomethyl)-5-methyl-5-n-undecyl-hydantoin
1,3-Bis(N-3'-methylpiperazinomethyl)-5,5-di-n-butyl hydantoin
1,3-Bis(N-methyl-ethylaminomethyl)-5,5-dimethyl hydantoin
1,3-Bis(N-methyl-n-butylaminomethyl)-5-methyl-5-n-butyl hydantoin
1,3-Bis(N-methyl-isooctylaminomethyl)-5-methyl-5-isobutyl hydantoin
1,3-Bis(N-methyl-n-decylaminomethyl)-5-methyl-5-n-undecyl hydantoin
1,3-Bis(N-methyl-n- dodecylaminomethyl)-5,5-di-n-butyl hydantoin
1,3-Bis(N-methyl-n-octadecylaminomethyl)-5,5-di-n-octyl hydantoin

R=ALKYL, R¹=ALKENYL 3-(Diethylaminomethyl)-5-methyl-5-(4'-methyl-3'-pentenyl-1')hydantoin
3-(Dibutylaminomethyl)-5-methyl-5-(4'-methyl-3'-pentenyl-1')hydantoin
3-(Di-n-octylaminomethyl)-5-methyl-5-(3'-methyl-2'-butenyl-1')hydantoin
3-(Di-n-tetradecylaminomethyl)-5-methyl-5-(3'-methyl-2'-butenyl-1')hydantoin
3-(Dicyclohexylaminomethyl)-5-methyl-5-(1'-methylpropenyl-1')hydantoin
3-(N-Piperidinomethyl)-5-methyl-5-(1'-methylpropenyl-1')hydantoin
3-(N-Methyl-n-butylaminomethyl)-5-methyl-5(4'-methyl-3'-pentenyl-1')hydantoin
3-(N-Methyl-isodecylaminomethyl)-5-methyl-5(3'-methyl-2'-butenyl-1')hydantoin 3-(N-Methyl-n-octadecylaminomethyl)-5-methyl-5(1'-methylpropenyl-1')hydantoin
1,3-Bis(di-n-butylaminomethyl)-5-methyl-5-(4'-methyl-3'-pentenyl-1')hydantoin
1,3-Bis(di-n-hexylaminomethyl)-5-methyl-5-(4'-methyl-3'-pentenyl-1')hydantoin
1,3-Bis(di-n-tetradecylaminomethyl)-5-methyl-5(4'-methyl-3'-pentenyl-1')hydantoin
1,3-Bis(diallylaminomethyl)-5-methyl-5-(3'-methyl-2'-butenyl-1')hydantoin
1,3-Bis(dicyclohexylaminomethyl)-5-methyl-5-(3'-methyl-2'-butenyl-1')hydantoin
1,3-Bis(N-piperidinomethyl)-5-methyl-5-(1'-methylpropenyl-1')hydantoin
1,3-Bis(N-morpholinomethyl)-5-methyl-5-(1'-methylpropenyl-1')hydantoin
1,3-Bis(N-methyl-n-propylaminomethyl)-5-methyl-5-(4'-methyl-3'-pentenyl-1')hydantoin
1,3-Bis(N-methyl-isohexylaminomethyl)-5-methyl-5-(3'-methyl-2'-butenyl-1')hydantoin
1,3-Bis(N-methyl-n-dodecylaminomethyl)-5-methyl-5-(1'-methylpropenyl-1')hydantoin

R=ALKYL, R¹=CYCLOALKYL 3-(Di-n-butylaminomethyl)-5-methyl-5-cyclopropylhydantoin
3-(Di-n-octylaminomethyl)-5-methyl-5-cyclopropylhydantoin
3-(Di-n-decylaminomethyl)-5-methyl-5-cyclobutylhydantoin
3-(Di-n-tetradecylaminomethyl)-5-methyl-5-cyclopentylhydantoin
3-(Diallylaminomethyl)-5-methyl-5-cyclopentylhydantoin
3-(Dicyclohexylaminomethyl)-5-methyl-5-cyclohexylhydantoin
3-(Dicyclohexylaminomethyl)-5-methyl-5-cyclooctylhydantoin
3-(N-Pyrrolidinomethyl)-5-methyl-5-cyclododecylhydantoin
3-(N-methyl-isobutylaminomethyl)-5-methyl-5-cyclopropyl hydantoin
3-(N-methyl-n-octylaminomethyl)-5-methyl-5-cyclobutyl hydantoin
3-(N-methyl-n-undecylaminomethyl)-5-methyl-5-cyclohexyl hydantoin
3-(N-methyl-n-octadecylaminomethyl)-5-methyl-5-cyclooctyl hydantoin
1,3-Bis(di-methylaminomethyl)-5-methyl-5-cyclopropylhydantoin
1,3-Bis(diethylaminomethyl)-5-methyl-5-cyclopropyl hydantoin
1,3-Bis(di-n-propylaminomethyl)-5-methyl-5-cyclobutyl hydantoin
1,3-Bis(di-n-butylaminomethyl)-5-methyl-5-cyclopentyl hydantoin
1,3-Bis(di-isobutylaminomethyl)-5-methyl-5-cyclopentyl hydantoin
1,3-Bis(di-n-hexylaminomethyl)-5-methyl-5-cyclopropyl hydantoin
1,3-Bis(di-n-octylaminomethyl)-5-methyl-5-cyclopropyl hydantoin
1,3-Bis(di-n-decylaminomethyl)-5-methyl-5-cyclohexyl hydantoin
1,3-Bis(di-n-dodecylaminomethyl)-5-methyl-5-cyclohexyl hydantoin
1,3-Bis(di-allylaminomethyl)-5-methyl-5-cyclohexyl hydantoin
1,3-Bis(N-methyl-n-propylaminomethyl)-5-methyl-5-cyclohexyl hydantoin
1,3-Bis(N-methyl-n-pentylaminomethyl)-5-methyl-5-cyclopentyl hydantoin
1,3-Bis(N-methyl-n-heptylaminomethyl)-5-methyl-5-cyclobutyl hydantoin
1,3-Bis(N-methyl-n-nonylaminomethyl)-5-methyl-5-cyclopentyl hydantoin

R=ALKYL, R¹=ARYL 3-(Diethylaminomethyl)-5-methyl-5-phenylhydantoin
3-(Di-isobutylaminomethyl)-5-ethyl-5-phenylhydantoin
3-(Di-n-octylaminomethyl)-5-n-propyl-5-phenylhydantoin
3-(Di-n-tetradecylaminomethyl)-5-methyl-5-α-naphthylhydantoin
3-(Di-allylaminomethyl)-5-methyl-5-(4'-methylphenyl)hydantoin
3-(Di-cyclopentylaminomethyl)-5-methyl-5-(2'-chlorophenyl)hydantoin
3-(Di-cyclohexylaminomethyl)-5-methyl-5-(4'-methoxyphenyl)hydantoin
3-(N-Pyrrolidinomethyl)-5-methyl-5-(2',4'-dichlorophenyl)hydantoin
3-(N-Morpholinomethyl)-5-methyl-5-(2'-butoxyphenyl)hydantoin
3-(N-3'-Methylpiperazinomethyl)-5-methyl-5-α-naphthylhydantoin
3-(N-Methyl-ethylaminomethyl)-5-methyl-5-α-naphthyl hydantoin
3-(N-Methyl-n-butylaminoethyl)-5-methyl-5-phenyl hydantoin
3-(N-Methyl-isohexylaminomethyl)-5-methyl-5-(4'-methylphenyl)hydantoin
3-(N-Methyl-n-octylaminomethyl)-5-methyl-5-(4'-methoxyphenyl)hydantoin
3-(N-Methyl-n-octadecylaminomethyl)-5-methyl-5-β-naphthyl hydantoin

R=ALKYL, R¹=ARALKYL 3-(Di-n-hexylaminomethyl)-5-methyl-5-benzylhydantoin
3-(Di-2'-ethylhexylaminomethyl)-5-methyl-5-α-naphthylmethyl-hydantoin
3-(Diallylaminomethyl)-5-methyl-5-(3'-chlorobenzyl)hydantoin
3-(Dicyclopentylaminomethyl)-5-methyl-5-β-naphthylmethyl hydantoin
3-(N-Piperidinomethyl)-5-ethyl-5-benzylhydantoin
3-(N-Methylaminomethyl)-5-methyl-5-β-naphthylmethyl hydantoin
3-(N-Methyl-isohexylaminomethyl)-5-methyl-5-α-naphthylmethyl hydantoin
3-(N-Methyl-n-nonylaminomethyl)-5-methyl-5-(4'-chlorobenzyl)hydantoin
3-(N-Methyl-n-dodecylaminomethyl)-5-methyl-5-benzyl hydantoin

R=R¹=CYCLOALKYL 3-(Di-n-propylaminomethyl)-5,5-di-cyclohexyl hydantoin
3-(Di-n-hexylaminomethyl)-5,5-di-cyclooctyl hydantoin
3-(Di-n-dodecylaminomethyl)-5-cyclohexyl-5-(4'-methylcyclohexyl)hydantoin 3-(Di-n-tetradecylaminomethyl)-5,5-di(4'-methylcyclohexyl)hydantoin 3-(Di-n-tetradecylaminomethyl)-5,5-di-(4'-methylcyclohexyl)hydantoin 3-(Diallylaminomethyl)-5-cyclohexyl-5-(3'-methylcyclohexyl)hydantoin 3-(Dicyclohexylaminomethyl)-5,5-di-(3'-methylcyclohexyl)hydantoin 3-(N-Pyrrolidinomethyl)-5-cyclohexyl-5-(3',5'-dimethylcyclohexyl)hydantoin 3-(N-Morpholinomethyl)-5,5-di-(3',5'-dimethylcyclohexyl)hydantoin 3-(N-Methyl-n-propylaminomethyl)-5,5-dicyclohexyl hydantoin 3-(N-Methyl-isooctylaminomethyl)-5-cyclohexyl-5-(4'-methylcyclohexyl)hydantoin 3-(N-Methyl-n-octadecylaminomethyl)-5,5-di(4'-methylcyclohexyl)hydantoin

R=CYCLOALKYL, R¹=ARYL 3-(Di-ethylaminomethyl)-5-cyclohexyl-5-phenyl-hydantoin 3-(Di-isobutylaminomethyl)-5-cyclohexyl-5-(4'-methylphenyl)hydantoin 3-(Di-n-octylaminomethyl)-5-(3'-methylcyclohexyl)-5-phenyl hydantoin 3-(Di-n-tetradecylaminomethyl)-5-(3',5'-dimethylcyclohexyl)-5-phenylhydantoin 3-(Di-allylaminomethyl)-5-cyclohexyl-5-(4'-methoxyphenyl)hydantoin 3-(Di-cyclopentylaminomethyl)-5-cyclohexyl-5-(2',4'-dichlorophenyl)hydantoin 3-(N-Piperidinomethyl)-5-(3',5'-dimethylcyclohexyl)-5-(4'-methylphenyl)hydantoin 3-(N-Methyl-isobutylaminomethyl)-5-cyclohexyl-5-phenyl hydantoin 3-(N-Methyl-n-octylaminomethyl)-5-cyclohexyl-5-(4'-methylphenyl)hydantoin 3-(N-Methyl-n-dodecylaminomethyl)-5-(4'-methylcyclohexyl)-5-phenyl hydantoin

R=CYCLOALKYL, R¹=ARALKYL 3-(Dimethylaminomethyl)-5-cyclohexyl-5-benzyl-hydantoin 3-(Di-n-hexylaminomethyl)-5-cyclohexyl-5-α-naphthylmethyl-hydantoin 3-(Di-n-decylaminomethyl)-5-cyclohexyl-5-(4'-methylbenzyl)hydantoin 3-(Di-n-tetradecylaminomethyl)-5-(4'-methylcyclohexyl)-5-benzyl hydantoin 3-(Diallylaminomethyl)-5-(3',5'-dimethylcyclohexyl)-5-(4'-chlorobenzyl)hydantoin 3-(Dicyclohexylaminomethyl)-5-(3',5'-dimethylcyclohexyl)-5-(4'-methoxybenzyl)hydantoin 3-(N-Pyrrolidinomethyl)-5-(4'-methylcyclohexyl)-5-(2',4'-dichlorobenzyl)hydantoin 3-(N-Methyl-n-butylaminomethyl)-5-cyclohexyl-5-benzyl hydantoin 3-(N-Methyl-n-heptylaminomethyl)-5-cyclohexyl-5-(4'-chlorobenzyl)hydantoin 3-(N-Methyl-isodecylaminomethyl)-5-(4'-methylcyclohexyl)-5-benzyl hydantoin 3-(N-Methyl-n-undecylaminomethyl)-5-cyclohexyl-5-α-naphthylmethyl hydantoin

R=R¹=ARYL 3-(Di-n-propylaminomethyl)-5,5-diphenylhydantoin 3-(Di-isohexylaminomethyl)-5-phenyl-5-(4'-methylphenyl)hydantoin 3-(Di-n-octylaminomethyl)-5-phenyl-5-(4'-methoxyphenyl)hydantoin 3-(Di-n-tetradecylaminomethyl)-5-phenyl-5-(2',4'-dimethoxyphenyl)hydantoin 3-(Diallylaminomethyl)-5-phenyl-5-(2',4'-dichlorophenyl)hydantoin 3-(Dicyclopentylaminomethyl)-5-(4'-methylphenyl)-5-(4'-methoxyphenyl)hydantoin 3-(Dicyclohexylaminomethyl)-5-(4'-methoxyphenyl)-5-(2',4'-dichlorophenyl)hydantoin 3-(N-Piperidinomethyl)-5,5-di-(4'-chlorophenyl)hydantoin 3-(N-Morpholinomethyl)-5,5-di-(4'-methylphenyl)hydantoin 3-(N-Methyl-ethylaminomethyl)-5,5-di-(4'-methoxyphenyl)hydantoin 3-(N-Methyl-isohexylaminomethyl)-5,5-di-(4'-chlorophenyl)hydantoin 3-(N-Methyl-n-decylaminomethyl)-5-phenyl-5-(4'-methylphenyl)hydantoin 3-(N-Methyl-n-tetradecylaminomethyl)-5-(4'-chlorophenyl)-5-(4'-methylphenyl)hydantoin

R=ARYL, R'=ARALKYL 3-(Di-isobutylaminomethyl)-5-phenyl-5-benzyl hydantoin 3-(Di-2'-ethylhexylaminomethyl)-5-(4'-methylphenyl)-5-benzyl hydantoin 3-(Di-n-decylaminomethyl)-5-(4'-methylphenyl)-5-(4'-methylbenzyl)hydantoin 3-(Di-n-tetradecylaminomethyl)-5-(4'-methoxyphenyl)-5-benzyl hydantoin 3-(Di-cyclohexylaminomethyl)-5-(4'-chlorophenyl)-5-(4'-methylbenzyl)hydantoin 3-(N-Pyrrolidinomethyl)-5-(4'-chlorophenyl)-5-(4'-chlorobenzyl)hydantoin 3-(N-Methyl-n-propylaminomethyl)-5-phenyl-5-benzyl hydantoin 3-(N-Methyl-n-heptylaminomethyl)-5-phenyl-5-(4'-methylbenzyl) hydantoin 3-(N-Methyl-n-undecylaminomethyl)-5-(4'-chlorophenyl)-5-(4'-chlorobenzyl)hydantoin

R AND R¹ FORM A CARBOCYCLIC RING 3-(Dimethylaminomethyl)-5,5-cyclotetramethylene hydantoin 3-(Di-n-butylaminomethyl)-5,5-2'-methylcyclotetramethylene hydantoin 3-(Di-isobutylaminomethyl)-5,5-cyclopertamethylene hydantoin 3-(Di-n-hexylaminomethyl)-5,5-2'-methylcyclopentamethylene hydantoin 3-(Di-2¹-ethylhexylaminomethyl)-5,5-3'-methylcyclopentamethylene hydantoin 3-(Di-n-tetradecylaminomethyl)-5,5-cyclohexamethylene hydantoin 3-(Diallylaminomethyl)-5,5-cycloheptamethylene hydantoin 3-(Dicyclohexylaminomethyl)-5,5-cycloundecamethylene hydantoin 3-(N-Pyrrolidinomethyl)-5,5-1',3'-dimethylcyclopentamethylene hydantoin 3-(N-Piperidinomethyl)-5,5-1',4'-dimethylcyclopentamethylene hydantoin 3-(N-Morpholinomethyl)-5,5-2',4'-dimethylcyclopentamethylene hydantoin 3-(N-3'-Methylpiperazinomethyl)-5,5-4'-methyliso-
propylcyclopentamethylene hydantoin 3-(N-Methyl-isobutylaminomethyl)-5,5-cyclotet-
ramethylene hydantoin 3-(N-Methyl-n-octylaminomethyl)-5,5-cyclopen-
tamethylene hydantoin 3-(N-Methyl-isodecylaminomethyl)-5,5-cyclohex-
amethylene hydantoin 3-(N-Methyl-n-dodecylaminomethyl)-5,5,2'-methyl-
cyclotetramethylene hydantoin 3-(N-Methyl-n-tetradecylaminomethyl)-5,5-3'-
methylcyclopentamethylene hydantoin 3-(N-Methyl-n-octadecylaminomethyl)-5,5-1',3'-
dimethylcyclopentamethylene hydantoin 1,3-Bis(dimethylaminomethyl)-5,5-cyclotetramethy-
lene hydantoin 1,3-Bis(diethylaminomethyl)-5,5-cyclopentamethy-
lene hydantoin 1,3-Bis(di-n-propylaminomethyl)-5,5-cyclotet-
ramethylene hydantoin 1,3-Bis(di-n-butylaminomethyl)-5,5-cyclopen-
tamethylene hydantoin 1,3-Bis(di-n-hexylaminomethyl)-5,5-cyclotet-
ramethylene hydantoin 1,3-Bis(di-n-octylaminomethyl)-5,5-cyclopen-
tamethylene hydantoin 1,3-Bis(N-methyl-n-propylaminomethyl)-5,5-
cyclotetramethylene hydantoin 1,3-Bis(N-methyl-n-hexylaminomethyl)-5,5-
cyclopentamethylene hydantoin 1,3-Bis(N-methyl-n-octylaminomethyl)-5,5-cyclotet-
ramethylene hydantoin

R AND R¹ FORM A HETEROCYCLIC RING 3-(Di-n-butylaminomethyl)-1,3,8-triazaspirodecane-
2,4-dione 3-(Di-isooctylaminomethyl)-8-methyl-1,3,8-triazas-
pirodecane-2,4-dione 3-(Di-n-dodecylaminomethyl)-7,7,9,9-tetramethyl-
1,3,8-triazaspirodecane-2,4-dione 3-(Di-allylaminomethyl)-7,7,8,9,9-pentamethyl-1,3,8-
triazaspirodecane-2,4-dione 3-(Di-cyclopentylaminomethyl)-1,3,8-triazaoxaspiro-
decane-2,4-dione 3-(Di-cyclohexylaminomethyl)-7-methyl-1,3,8-
diazaoxaspirodecane-2,4-dione 3-(N-Piperidinomethyl)-1,3,8-diazathiaspirodecane-
2,4-dione 3-(N-Methyl-n-octadecylaminomethyl)-1,3,8-triazas-
pirodecane-2,4-dione 3-(N-Methyl-isooctylaminomethyl)-7,8,9-trimethyl-
1,3,8-triazaspirodecane-2,4-dione 3-(N-Methyl-n-propylaminomethyl)-7,7,9,9-tet-
ramethyl-1,3,8-triazaspirodecane-2,4-dione 1,3-Bis(diethylaminomethyl)-7,7,8,9,9-pentamethyl-
1,3,8-triazaspirodecane-2,4-dione 1,3-Bis(di-n-butylaminomethyl)-8-methyl-1,3,8-
triazaspirodecane-2,4-dione 1,3-Bis(di-n-hexylaminomethyl)-1,3,8-triazaspirodec-
ane-2,4-dione 1,3-Bis(N-methyl-n-propylaminomethyl)-1,3,8-
triazaspirodecane-2,4-dione Other specific compounds of formula I are e.g.

3-(dimethoxyphosphonoethyl)-5,5-dimethyl hydan-
toin 3-(diethoxyphosphono-n-butyl)-5,5-dimethyl hydan-
toin 3-(diethoxyphosphonoethyl)-5-methyl-5-ethyl hy-
dantoin 3-(diethoxyphosphono-n-hexyl)-5,5-dimethyl hydan-
toin 3-(diethoxyphosphonoethyl)-5,5-dimethyl hydantoin In the above list of specific compounds one or both of the oxygen atoms may be replaced by sulphur to give the analogous 2-thio-, 4-thio or 2,4-dithiohydantoins.

With respect to compounds of formula I preferably at least one, and more preferably both of X and Y are sulphur atoms.

In formula I, when $R^2$ and $R^3$ are both hydrogen, R and $R^1$ are preferably straight or branched chain alkyl containing from 1 to 8 carbon atoms or R and $R^1$ together with the carbon to which they are attached form a saturated carbocyclic ring containing from 5 to 12 carbon atoms.

In formula I when $R^2$ and/or $R^3$ are dihydrocarbylaminomethyl groups:

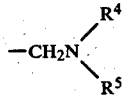

$R^4$ and $R^5$ are preferably straight or branched chain alkyl groups containing from 2 to 12 carbon atoms. More preferred are those compounds wherein $R^4$ and $R^5$ are the same and are straight or branched chain alkyl groups containing from 2 to 12 carbon atoms.

All the compounds of formula I wherein $R^2$ and $R^3$ are each a dihydrocarbylaminomethyl group (i.e. compounds of formula IA) are novel per se and, as such, form part of the present invention:

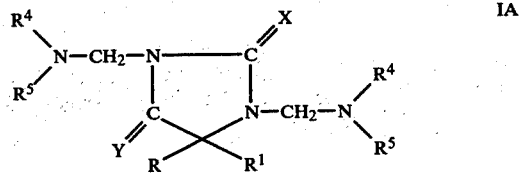

wherein X, Y, R, $R^1$, $R^4$ and $R^5$ have their previous significance.

Many of the compounds of formula I wherein $R^2$ is a dihydrocarbylaminomethyl group and $R^3$ is hydrogen (i.e. compounds of formula IB) are novel:

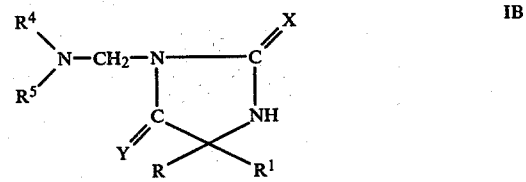

wherein X, Y, R, $R^1$, $R^4$ and $R^5$ have their previous significance.

However, the following compounds, falling within the general formula IB, have been described but not for use in lubricating oils [i.e. in J. Chem. Soc. 1947, pages 681–3 Farm.zh.(Kiev)24(2) 18–22 (1969) Tetrahedron 15, 93 (1961) and Dissertations Pharmaceutical et Pharmacological 20(5) 507–37(1968)].

| R | R¹ | R⁴ | R⁵ | X | Y |
|---|---|---|---|---|---|
| H | H | H | ⌬ (phenyl) | S | O |
| H | H | H | o-CH₃-C₆H₄ | S | O |
| H | H | H | m-CH₃-C₆H₄ | S | O |
| H | H | H | p-CH₃-C₆H₄ | S | O |
| H | H | H | p-H₅C₂O-C₆H₄ | S | O |
| H | H | H | p-Br-C₆H₄ | S | O |
| H | H | —CH₂CH₂OCH₂CH₂— | | S | O |
| H | H | —CH₂CH₂NHCH₂CH₂— | | S | O |
| H | H | —(CH₂)₅— | | S | O |
| H | H | —CH₂CH₂OCH₂CH₂— | | O | O |
| CH₃ | CH₃ | —CH₂CH₂OCH₂CH₂— | | O | O |
| CH₃ | CH₃ | —(CH₂)₅— | | O | O |
| —(CH₂)₅— | | —CH₂CH₂OCH₂CH₂— | | O | O |
| —(CH₂)₅— | | —(CH₂)₅— | | O | O |
| C₆H₅ | C₆H₅ | —CH₂CH₂N(CH₃)CH₂CH₂— | | O | O |
| C₆H₅ | C₆H₅ | —CH₂CH₂N(CH₃)CH₂CH₂— | | S | O |
| —(CH₂)₅— | | —CH₂CH₂N(CH₃)CH₂CH₂— | | O | O |
| C₆H₅ | C₆H₅ | —CH₂CH₂OCH₂CH₂— | | S | S |
| C₆H₅ | C₆H₅ | —(CH₂)₅— | | S | S |
| C₆H₅ | C₆H₅ | —(CH₂)₄— | | S | S |

Many of the compounds of formula I wherein R² and R³ are each hydrogen and X and Y are each sulphur (i.e. compounds of formula IC) are novel:

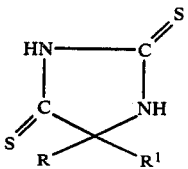

IC wherein R and R¹ have their previous significance. However, the following compounds, falling within the general formula IC, have been described but not for use in lubricating oils.

| R | R¹ |
|---|---|
| CH₃ | CH₃ |
| CH₃ | C₂H₅ |
| C₂H₅ | C₂H₅ |
| CH₃ | n-C₃H₇ |
| CH₃ | iso C₃H₇ |
| CH₃ | iso C₄H₉ |
| CH₃ | t-C₄H₉ |
| CH₃ | n-C₅H₁₁ |
| CH₃ | —CH₂CH₂CH=C(CH₃)₂ |
| CH₃ | cyclohexyl |
| CH₃ | —CH₂-C₆H₅ |
| CH₃ | —CH₂CH₂-C₆H₅ |
| | —(CH₂)₄— |
| | —CH₂CH(CH₃)CH₂— |
| | —(CH₂)₅— |
| | —CH₂CH(CH₃)(CH₂)₄— |
| | —CH₂CH(CH₃)(CH₂)₃— |
| | —(CH₂)₂CH(CH₃)(CH₂)₂— |
| | —(CH₂)₆— |
| | —CH(CH₃)CH₂CH(CH₃)CH₂CH₂— |
| | —CH(CH₃)CH₂CH₂CH(CH₃)CH₂— |
| | —CH₂CH(CH₃)CH₂CH(CH₃)CH₂— |
| | —CH(CH(CH₃)₂)CH₂CH₂CH(CH₃)CH₂— |
| H | H, C₆H₅ |

-continued

| R | R¹ |
|---|---|
|  |  |

The compounds of formula I wherein R² or R³ is a phosphonoalkyl group are not new, having been described e.g. in British Patent Specification No. 1,454,384, where also the preparation of such compounds is described.

The present invention therefore provides a process of producing compounds having the formulae:

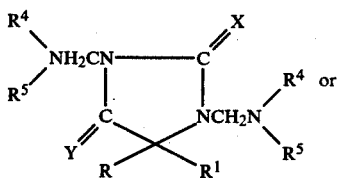         IA

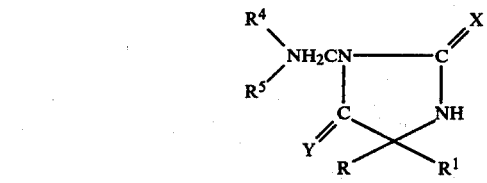         IB wherein X, Y, R, R¹, R⁴ and R⁵ have their previous significance, comprising reacting a compound having the formula:

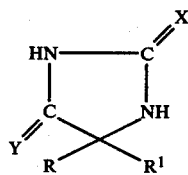         II wherein X, Y, R and R¹ have their previous significance, with formaldehyde and a secondary amine having the formula:

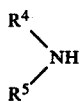         III wherein R⁴ and R⁵ have their previous significance.

The reaction of the compound of formula II with formaldehyde and the amine of formula III is conveniently carried out by heating all the reactants together at an elevated temperature e.g. a temperature in the range of from 50° to 120° C. The reaction may be carried out in a solvent, e.g. cyclohexane, toluene or ethyl alcohol. If desired, the compound of formula III and formaldehyde may be first reacted to form the corresponding N-methylol compound, prior to reaction with the compound of formula II.

The formaldehyde reactant is conveniently used in its commercially-available forms viz. formalin or paraformaldehyde.

Suitable examples of secondary amines III are:

| | |
|---|---|
| dimethylamine | di-(2-ethoxyethyl)amine |
| diethylamine | di-(2-chloroethyl)amine |
| di-n-propylamine | Di-cyclohexylamine |
| di-isopropylamine | Pyrrolidine |
| di-n-butylamine | Piperidine |
| di-sec.butylamine | Morpholine |
| di-n-pentylamine | N-methylpiperazine |
| di-n-hexylamine | N-methyl-n-butylamine |
| di-n-octylamine | N-methyl-n-octylamine |
| di-2-ethylhexylamine | N-methyl-isodecylamine |
| di-n-decylamine | N-methyl-n-octadecylamine |
| di-n-dodecylamine | |
| di-n-tetradecylamine | |
| di-n-octadecylamine | |
| di-allylamine | |

Preferred secondary amines III are those containing straight- or branched- chain alkyl groups having from 1 to 12 carbon atoms.

The present invention further provides a process of producing compounds having the formula:

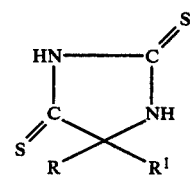         IC wherein R and R¹ have their previous significance, comprising reacting a hydantoin having the formula:

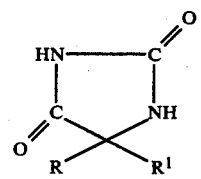         IV wherein R and R¹ have their previous significance, with a phosphorus sulphide, for example phosphorus trisulphide or phosphorus pentasulphide, in an inert solvent at an elevated temperature e.g. a temperature in the range from 80° to 250° C. Suitable solvents include dioxan, pyridine, toluene, xylene, or decalin.

The hydantoin starting-materials of formula IV are well-known and may be produced by processes well-known per se.

The compounds of formula IC may also be prepared by reacting a carbonyl containing compound of formula:

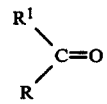         V wherein R and R¹ have their previous significance with carbon disulphide, an alkali metal cyanide, and an ammonium salt in a solvent system which preferably produces a homogeneous reaction mass at an elevated temperature. Suitable alkali metal cyanides are sodium cyanide or potassium cyanide, a suitable ammonium salt is ammonium chloride and a suitable solvent system is an aqueous alcoholic system e.g. aqueous methyl alcohol or aqueous ethyl alcohol. The reaction temperature may range from 40° C. to the reflux temperature of the solvent.

The lubricating oil compositions of the invention may, if desired, contain in addition other additives which are conventionally added to improve the properties thereof, such as antioxidants, rust and corrosion inhibitors, metal passivators and/or sulphur scavengers, viscosity index improvers/pour point depressants, dispersants/detergents, and extreme pressure/antiwear additives.

Examples of antioxidants are:
(a) Alkylated and non-alkylated aromatic amines and mixtures thereof, for example dioctyldiphenylamine; mono-t-octyl-phenyl-α- and β-naphthylamines; dioctylphenothiazine; phenyl-α-naphthylamine; N,N'-di-sec.butyl p-phenylenediamine.
(b) Hindered phenols, for example 2,6-ditertiarybutyl-p-cresol; 4,4'-bis-(2,6-di-t-butylphenol); 2,4,6-triisopropylphenol; 2,2'-thio-bis-(4-methyl-6-tertbutylphenol).
(c) Alkyl, aryl or alkarylphosphites, for example triphenylphosphite; trinonylphosphite; diphenyldecylphosphite.
(d) Esters of thiodipropionic acid, for example dilaurylthiodipropionate.
(e) Salts of carbamic and dithiophosphoric acids, for example antimony diamyldithiocarbamate, zinc diamyldithiophosphate
(f) Metal salts, complexes of organic chelating agents for example copper bis(trifluoroacetylacetonates), copper phthalocyanines, tributyl ester of EDTA, mono sodium salt.
(g) Free radical antioxidants for example nitroxides, etc.
(h) Combinations of two or more antioxidants from any of the above sections, for example an alkylated aromatic amine and a hindered phenol.

Examples of metal passivators and/or sulphur scavengers are:
(a) for copper, for example, 1,2,4-triazoles, benzotriazole, 5,5'-methylene-bisbenzotriazole, tetrahydrobenzotriazole or their derivatives, 2,5-dimercaptothiadiazole and derivatives thereof, salicylidenepropylenediamine, salts of salicylalaminoguadine;
(b) for magnesium, for example pyridylamines
(c) for lead, for example sebacic acid, quinizarin, propyl gallate
(d) combinations of two or more of the above additives.

Examples of rust and corrosion inhibitors are:
(a) Organic acids, and their esters, metal salts, anhydrides for example N-oleoyl sarcosine, sorbitan mono-oleate, lead naphthenate, dodecenylsuccinic anhydride.
(b) Nitrogen containing materials, for example
  i. primary, secondary or tertiary aliphatic or cycloaliphatic amines and amine salts of organic and inorganic acids, for example morpholine, stearyl amine, triethanolamine caprylate,
  ii. heterocyclic compounds, for example imidazolines, oxazolines.
(c) Phosphorus containing materials, for example inorganic phosphates, phosphonic acids, amine phosphates.
(d) Sulphur containing materials, for example barium dinonylnaphthalene sulphonates.
(e) Combinations of two or more of the above additives.

Examples of viscosity index improvers/pour point depressants are, for example:

polyacrylates, polybutenes, polyvinyl pyrrolidones, styrene-butadiene copolymers.

Examples of dispersant/detergents are, for example: metal sulphonates (Ca,Ba,Mg) and phenates, polybutenyl succinimides.

Examples of extreme pressure/antiwear additives are: sulphur and/or phosphorus and/or halogen containing materials, for example sulphurised sperm oil, zinc dialkyl phosphoro-dithioates, tritolylphosphate, chlorinated paraffins.

The present invention also provides a process of producing compositions of lubricating oils comprising 0.001% to 10% by weight of a compound having the formula I, which comprises admixing the lubricating oil with the compound having the formula I.

The following Examples further illustrate the present invention. Parts and percentages shown therein are by weight unless otherwise stated. Where the product is an oil, infra-red and NMR spectroscopic analyses confirmed that structures indicated by the respective elemental analyses.

EXAMPLE 1

6.40 Parts of 5,5-dimethylhydantoin, 24.10 parts of di-n-octylamine and 3.15 parts of paraformaldehyde were refluxed in 200 parts of cyclohexane for 14 hours, the water of reaction being collected in a Dean and Stark water separator. The solution was then cooled and the cyclohexane solvent removed under reduced pressure at 60°. The residue was filtered through Hyflo(a commercially-available filter aid) to give 30.7 parts of 1,3-bis(di-n-octylaminomethyl)-5,5-dimethyl hydantoin as a colourless oil having the following elemental analysis:

$C_{39}H_{78}N_4O_2$ requires: C, 73.75%; H, 12.38%; N, 8.82%; found: C, 73.75%; H, 12.61%; N, 8.77%

Using the above procedure the following compounds described in Examples 2 to 45 were prepared

EXAMPLE 2

1,3-Bis-(di-n-butylaminomethyl)-5,5-cyclopentamethylene-2,4-dithiohydantoin.

$C_{18}H_{32}N_4S_2$ requires: C, 64.67%; H, 10.43%; N, 11.60%; S, 13.28%; found: C, 64.61%; H, 10.69%; N, 11.42%; S, 13.25%

EXAMPLE 3

1,3-Bis-(di-n-butylaminomethyl)-5,5-dimethyl-2,4-dithiohydantoin.

$C_{23}H_{46}N_4S_2$ requires: C, 62.39%; H, 10.47%; N, 12.66%; S, 14.48%; found: C, 62.44%; H, 10.67%; N, 12.74%; S, 14.58%

EXAMPLE 4

1,3-Bis-(di-n-octylaminomethyl)-5,5-dimethyl-2,4-dithiohydantoin $C_{39}H_{78}N_4S_2$ requires: C, 70.27%; H, 11.71%; N, 8.41%; S, 9.61%; found: C, 71.70%; H, 12.01%; N, 8.43%; S, 9.58%

EXAMPLE 5

1,3-Bis-(di-n-butylaminomethyl)-5,5-cyclotetramethylene-2,4-dithiohydantoin $C_{25}H_{48}N_4S_2$ requires: C, 64.10%; H, 10.25%; N, 11.97%; S, 13.68%; found: C, 64.02%; H, 10.36%; N, 12.17%; S, 15.08%

EXAMPLE 6

1,3-Bis(di-n-butylaminomethyl)-5,5-di-n-butyl-2,4-dithiohydantoin $C_{29}H_{58}N_4S_2$ requires: C, 66.09%; H, 11.09%; N, 10.93%; S, 12.16%; found: C, 66.29%; H, 11.35%; N, 10.49%; S, 12.06%

EXAMPLE 7

1,3-Bis-(di-n-butylaminomethyl)hydantoin $C_{21}H_{42}N_4O_2$ requires: C, 65.92%; H, 11.06%; N, 14.64%; found: C, 65.73%; H, 11.31%; N, 14.38%

EXAMPLE 8

1,3-Bis(di-n-octylaminomethyl)-5,5-di-n-butyl-2,4-dithiohydantoin $C_{45}H_{90}N_4S_2$ requires: C, 71.93%; H, 12.07%; N, 7.45%; S, 8.53%; found: C, 72.06%; H, 12.40%; N, 7.55%; S, 8.26%

EXAMPLE 9

1,3-Bis(di-2-ethylhexylaminomethyl)hydantoin $C_{37}H_{74}N_4O_2$ requires: C, 73.19%; H, 12.29%; N, 9.23%; found: C, 73.35%; H, 12.35%; N, 8.81%

EXAMPLE 10

1,3-Bis(di-n-tetradecylaminomethyl)hydantoin $C_{61}H_{122}N_4O_2$ requires: C, 77.71%; H, 12.95%; N, 5.95%; found: C, 78.63%; H, 12.86%; N, 6.12%

EXAMPLE 11

1,3-Bis(diethylaminomethyl)-5,5-dimethyl hydantoin $C_{15}H_{30}N_4O_2$ requires: C, 60.37%; H, 10.13%; N, 18.78%; found: C, 60.82%; H, 10.33%; N, 18.40%

EXAMPLE 12

1,3-Bis(di-n-butylaminomethyl)-5,5-dimethyl hydantoin $C_{23}H_{46}N_4O_2$ requires: C, 67.32%; H, 11.22%; N, 13.66%; found: C, 67.00%; H, 11.12%; N, 13.69%

EXAMPLE 13

1,3-Bis(di-n-butylaminomethyl)-5,5-dimethyl-2-thiohydantoin $C_{23}H_{46}N_4OS$ requires: C, 64.73%; H, 10.86%; N, 13.13%; S, 7.51%; found: C, 64.58%; H, 11.31%; N, 12.93%; S, 7.31%

EXAMPLE 14

1,3-Bis(dicyclohexylaminomethyl)-5,5-dimethyl hydantoin $C_{31}H_{54}N_2O_2$ requires: C, 72.32%; H, 10.57%; N, 10.88%; found: C, 71.70%; H, 11.00%; N, 11.00%

EXAMPLE 15

1,3-Bis(dibenzylaminomethyl)-5,5-dimethyl-2,4-dithiohydantoin $C_{35}H_{38}N_4S_2$ requires: C, 72.62%; H, 6.62%; N, 9.68%; S, 11.08%; found: C, 71.83%; H, 6.84%; N, 9.84%; S, 11.54%

EXAMPLE 16

1,3-Bis(piperidinomethyl)-5,5-dimethyl hydantoin $C_{17}H_{30}N_4O_2$ requires: C, 63.31%; H, 9.38%; N, 17.37%; found: C, 63.09%; H, 9.49%; N, 17.09%

EXAMPLE 17

1,3-Bis(di-n-hexylaminomethyl)-5-methyl-5-ethyl hydantoin $C_{32}H_{64}N_4O_2$ requires: C, 71.58%; H, 12.02%; N, 10.44%; found: C, 71.38%; H, 11.98%; N, 10.68%

EXAMPLE 18

1,3-Bis(pyrrolidinomethyl)-5-methyl-5-ethyl-2,4-dithiohydantoin $C_{16}H_{28}N_4S_2$ requires: C, 56.47%; H, 8.24%; N, 16.47%; S, 18.82%; found: C, 56.10%; H, 8.37%; N, 16.06%; S, 18.83%

EXAMPLE 19

1,3-Bis(di-isobutylaminomethyl)-5-methyl-5-isobutyl hydantoin $C_{26}H_{52}N_4O_2$ requires: C, 68.98%; H, 11.58%; N, 12.34%; found: C, 68.74%; H, 11.25%; N, 12.61%

EXAMPLE 20

1,3-Bis(di-n-butylaminomethyl)-5-methyl-5-n-nonyl hydantoin $C_{31}H_{62}N_4O_2$ requires: C, 71.22%; H, 11.95%; N, 10.72%; found: C, 71.18%; H, 11.61%; N, 10.75%

EXAMPLE 21

1,3-Bis(di-n-butylaminomethyl)-5-phenyl hydantoin $C_{27}H_{46}N_4O_2$ requires: C, 70.54%; H, 10.30%; N, 12.19%; found: C, 70.75%; H, 10.31%; N, 12.20%

EXAMPLE 22

1,3-Bis(di-n-butylaminomethyl)-5-phenyl-2-thiohydantoin $C_{27}H_{46}N_4OS$ requires: C, 68.30%; H, 9.77%; N, 11.80%; S, 6.75%; found: C, 67.42%; H, 9.06%; N, 11.43%; S, 5.90%

EXAMPLE 23

1,3-Bis(diethylaminomethyl)-5-methyl-5-ethyl hydantoin $C_{16}H_{32}N_4O_2$ requires: C, 61.50%; H, 10.32%; N, 17.94%; found: C, 61.30%, H, 10.55%; N, 17.34%

EXAMPLE 24

3-(Di-2-ethylhexylaminomethyl)-5,5-dimethyl-2-thiohydantoin $C_{22}H_{43}N_3OS$ requires: C, 66.44%; H, 10.89%; N, 10.57%; S, 8.06%; found: C, 68.52%; H, 11.38%; N, 9.53%; S, 7.18%

EXAMPLE 25

3-(Di-2-ethylhexylaminomethyl)-5,5-dimethyl-2,4-dithiohydantoin $C_{22}H_{43}N_3S_2$ requires: C, 63.86%; H, 10.47%; N, 10.15%; S, 15.49%; found: C, 63.98%; H, 10.49%; N, 9.98%; S, 15.31%

EXAMPLE 26

3-(Piperidinomethyl)-5-methyl-5-n-nonyl hydantoin $C_{19}H_{35}N_3O_2$ requires: C, 67.61%; H, 10.45%; N, 12.45%; found: C, 67.54%; H, 10.36%; N, 12.42%

EXAMPLE 27

3-(Di-2-ethylhexylaminomethyl)-5,5-cyclopentamethylene-2,4-dithiohydantoin $C_{25}H_{47}N_3S_2$ requires: C, 66.23%; H, 10.38%; N, 9.27%; S, 14.13%; found: C, 66.93%; H, 10.75%; N, 9.31%; S, 13.63%

EXAMPLE 28

3-(Piperidinomethyl)-5,5-cyclopentamethylene hydantoin $C_{14}H_{23}N_3O_2$ requires: C, 63.40%; H, 8.68%; N, 15.85% found: C, 63.28%; H, 8.63%; N, 15.74%

EXAMPLE 29

3-(Dibenzylaminomethyl)-5,5-cyclopentamethylene hydantoin $C_{23}H_{27}N_3O_2$ requires: C, 73.18%; H, 7.21%; N, 11.13%; found: C, 72.88%; H, 7.16%; N, 11.16%

EXAMPLE 30

3-(Dicyclohexylaminomethyl)-5,5-3$^1$-methylcyclopentamethylene-2,4-dithiohydantoin $C_{22}H_{37}N_3S_2$ requires: C, 64.74%; H, 9.39%; N, 10.19%; S, 15.80%; found: C, 64.81%; H, 9.15%; N, 10.31%; S, 15.73%

EXAMPLE 31

3-(Di-2-ethylhexylaminomethyl)-5,5-cycloundecamethylene-2,4-dithiohydantoin $C_{31}H_{59}N_3S_2$ requires: C, 69.27%; H, 10.99%; N, 7.82%; S, 11.92%; found: C, 69.51%; H, 11.31%; N, 7.47%; S, 10.86%

EXAMPLE 32

1,3-Bis(di-n-tetradecylaminomethyl)-5-methyl-5-n-nonyl-2,4-dithiohydantoin $C_{71}H_{142}N_4S_2$ requires: C, 76.40%; H, 12.82%; N, 5.02%; S, 5.75%; found: C, 76.55%; H, 12.62%; N, 5.34%; S, 5.89%

EXAMPLE 33

1,3-Bis(N-methyl-n-butylaminomethyl)-5-methyl-5-ethyl-2,4-dithiohydantoin $C_{18}H_{36}N_4S_2$ requires: C, 58.01%; H, 9.74%; N, 15.04%; S, 17.21%; found: C, 58.22%; H, 9.81%; N, 15.24%; S, 17.08%

EXAMPLE 34

3-(Di-n-tetradecylaminomethyl)-5,5-diphenyl-2-thiohydantoin $C_{44}H_{71}N_3OS$ requires: C, 76.63%; H, 10.30%; N, 6.10%; S, 4.64%; found: C, 76.56%; H, 10.51%; N, 6.01%; S, 4.83%

EXAMPLE 35

3-(Di-n-octylaminomethyl)-5-ethyl-5-phenylhydantoin $C_{28}H_{47}N_3O_2$ requires: C, 73.47%; H, 10.35%; N, 9.18%; found: C, 75.46%; H, 10.83%; N, 9.46%

EXAMPLE 36

3-(N-Methyloctadecylaminomethyl)-5,5-diphenyl-2-thiohydantoin $C_{35}H_{53}N_3OS$ requires: C, 74.60%; H, 9.41%; N, 7.46%; S, 5.68%; found: C, 73.45%; H, 9.63%; N, 7.23%; S, 5.37%

EXAMPLE 37

1,3-Bis(morpholinomethyl)-5,5-dimethyl-2,4-dithiohydantoin $C_{15}H_{26}N_4O_2S_2$ requires: C, 50.25%; H, 7.31%; N, 15.63%; S, 17.88%; found: C, 50.34%; H, 7.47%; N, 15.47%; S, 17.47%

EXAMPLE 38

1,3-Bis(N-methyl-n-octadecylaminomethyl)-5,5-dimethyl-2,4-dithiohydantoin $C_{45}H_{90}N_4S_2$ requires: C, 71.93%; H, 12.07%; N, 7.46%; S, 8.53%; found: C, 70.53%; H, 12.05%; N, 6.99%; S, 8.25%

EXAMPLE 39

3-(N-Methyl-n-octadecylaminomethyl)-5,5-cyclopentamethylene-2,4-dithiohydantoin $C_{28}H_{53}N_3S_2$ requires: C, 67.82%; H, 10.77%; N, 8.48%; S, 12.93%; found: C, 67.44%; H, 11.71%; N, 8.42%; S, 12.53%

EXAMPLE 40

1,3-Bis(N-methyl-n-butylaminomethyl)-5-methyl-5-n-nonyl-2,4-dithiohydantoin $C_{25}H_{50}N_4S_2$ requires: C, 63.77%; H, 10.70%; N, 11.90%; S, 13.62%; found: C, 63.77%; H, 11.65%; N, 11.66%; S, 13.29%

EXAMPLE 41

3-(Di-2-ethylhexylaminomethyl)-5,5-3'-methylcyclopentamethylene-2,4-dithiohydantoin $C_{26}H_{49}N_3S_2$ requires: C, 66.75%; H, 10.56%; N, 8.98%; S, 13.71%; found: C, 67.18%; H, 10.93%; N, 9.13%; S, 13.39%

EXAMPLE 42

1,3-Bis(di-2-ethylhexylaminomethyl)-5-methyl-5-cyclopropyl-2,4-dithiohydantoin $C_{41}H_{80}N_4S_2$ requires: C, 71.03%; H, 11.63%; N, 8.08%; S, 9.25%; found: C, 70.05%; H, 11.84%; N, 7.47%; S, 8.86%

EXAMPLE 43

3-(Dicyclohexylaminomethyl)-5,5-cyclopentamethylene-2,4-dithiohydantoin $C_{21}H_{35}N_3S_2$ requires: C, 64.07%; H, 8.96%; N, 10.68%; S, 16.29%; found: C, 63.42%; H, 9.04%; N, 10.76%; S, 17.15%

EXAMPLE 44

1,3-Bis(dicyclohexylaminomethyl)-5-methyl-5-(4'-methyl-3'-pentyl-1')-2,4-dithiohydantoin $C_{36}H_{62}N_4S_2$ requires: C, 70.30%; H, 10.16%; N, 9.11%; S, 10.43%; found: C, 70.12%; H, 10.11%; N, 8.95%; S, 10.18%

EXAMPLE 45

3-(Di-n-octylaminomethyl)-5-phenyl-5-(4'-methylphenyl)hydantoin $C_{33}H_{49}N_3O_2$ requires: C, 76.25%; H, 9.50%; N, 8.09%; found: C, 74.96%; H, 9.76%; N, 7.68%

EXAMPLE 46

A solution of 29.0 parts of acetone, 25.5 parts of sodium cyanide, 27.5 parts of ammonium chloride and 38.0 parts of carbon disulphide in 150 parts of 50% aqueous methyl alcohol was gently refluxed at 55° C. to 60° C. for 20 hours. The reaction mass was then steam distilled and the residue allowed to cool. The solid, which crystallised from the solution was filtered and crystallised from aqueous methyl alcohol to yield 5,5-dimethyl-2,4-dithiohydantoin having a melting point of 144° C. and the following elemental analysis.

$C_5H_8N_2S_2$ requires: C, 37.50%; H, 5.00%; N, 17.45%; S, 40.00%; found: C, 37.72%; H, 5.16%; N, 17.44%; S, 40.05%;

Using the above procedure the following compounds described in Examples 47 to 58 were prepared.

EXAMPLE 47

5,5-Cyclotetramethylene-2,4-dithiohydantoin m.p.=245°–7° C.

$C_7H_{10}N_2S_2$ requires: C, 45.12%; H, 5.41%; N, 15.04%; S, 34.41%; found: C, 44.95%; H, 5.60%; N, 14.77%; S, 34.25%

EXAMPLE 48

5,5-Cyclopentamethylene-2,4-dithiohydantoin m.p.=269°–70° C.

$C_8H_{12}N_2S_2$ requires: C, 47.98%; H, 6.03%; N, 13.98%; S, 32.02%; found: C, 48.25%; H, 6.25%; N, 13.66%; S, 31.76%

EXAMPLE 49

5,5-3'-Methylcyclopentamethylene-2,4-dithiohydantoin m.p.=255° C.

$C_9H_{14}N_2S_2$ requires: C, 50.42%; H, 6.58%; N, 13.07%; S, 29.91%; found: C, 50.59%; H, 6.53%; N, 13.10%; S, 29.71%

EXAMPLE 50

5,5-Di-n-butyl-2,4-dithiohydantoin m.p.=162° C.

$C_{11}H_{20}N_2S_2$ requires: C, 54.05%; H, 8.24%; N, 11.46%; S, 26.23%; found: C, 54.06%; H, 8.32%; N, 11.34%; S, 26.45%

EXAMPLE 51

5,5-Cycloundecamethylene-2,4-dithiohydantoin m.p.=241° C.

$C_{14}H_{24}N_2S_2$ requires: C, 59.10%; H, 8.50%; N, 9.83%; S, 22.54%; found: C, 59.16%; H, 8.62%; N, 9.62%; S, 21.25%

EXAMPLE 52

5-Methyl-5-ethyl-2,4-dithiohydantoin m.p.=148°–9° C.

$C_6H_{10}N_2S_2$ requires: C, 41.35%; H, 5.75%; N, 16.08%; S, 36.79%; found: C, 41.69%; H, 5.84%; N, 16.00%; S, 36.64%

EXAMPLE 53

5-Methyl-5-(4'-methyl-3'-pententyl-1')-2,4-dithiohydantoin m.p.=97° C.

$C_{10}H_{16}N_2S_2$ requires: C, 52.63%; H, 7.02%; N, 12.28%; S, 28.07%; found: C, 52.79%; H, 7.42%; N, 12.09%; S, 28.72%

EXAMPLE 54

5-Methyl-5-cyclopropyl-2,4-dithiohydantoin m.p.=172°–3° C.

$C_7H_{10}N_2S_2$ requires: C, 45.16%; H, 5.38%; N, 15.05%; S, 34.41%; found: C, 45.90%; H, 5.57%; N, 14.99%; S, 34.35%

EXAMPLE 55

5-Benzyl-5-n-butyl-2,4-dithiohydantoin m.p.=199° C.

$C_{14}H_{18}N_2S_2$ requires: C, 60.39%; H, 6.52%; N, 10.06%; S, 23.03%; found: C, 61.19%; H, 6.84%; N, 10.06%; S, 22.84%

EXAMPLE 56

5,5-2',2',4'-Trimethylcyclopentamethylene-2,4-dithiohydantoin m.p.=221° C.

$C_{11}H_{18}N_2S_2$ requires: C, 54.50%; H, 7.49%; N, 11.56%; S, 26.45%; found: C, 54.46%; H, 7.65%; N, 11.55%; S, 26.30%

EXAMPLE 57

5-Methyl-5-isobutyl-2,4-dithiohydantoin m.p.=91°–2° C.

$C_8H_{14}N_2S_2$ requires: C, 47.49%; H, 6.97%; N, 13.85%; S, 31.69%; found: C, 47.71%; H, 7.14%; N, 13.59%; S, 31.51%

EXAMPLE 58

5,5,2'-Adamantyl-2,4-dithiohydantoin m.p.=290° C.

$C_{12}H_{16}N_2S_2$ requires: C, 57.10%; H, 6.39%; N, 11.10%; S, 25.41%; found: C, 57.19%; H, 6.67%; N, 10.88%; S, 25.70%

EXAMPLE 59

A mixture of 24.0 parts of 5-methyl-5-n-nonyl hydantoin and 44.4 parts of phosphorus pentasulphide was refluxed for 12 hours in 400 ml of toluene. The hot solution was filtered and the toluene solvent removed on a rotary evaporator at 60° C. The residue was chromatographed on a silica column using ethyl acetate as the effluent. The material from the column, after removing the ethyl acetate solvent on a rotary evaporator at 60° C., was crystallised from 60°–80° C. petroleum ether to yield 5-methyl-5-n-nonyl-2,4-dithiohydantoin having a melting point of 88°–9° C. and the following elemental analysis.

$C_{13}H_{24}N_2S_2$ requires: C, 57.30%; H, 8.88%; N, 10.28%; S, 23.53%; found: C, 57.59%; H, 8.99%; N, 10.36%; S, 23.60%

Using the above procedure the following compounds described in Examples 60 to 62 were prepared.

EXAMPLE 60

5,5-Di-n-octyl-2,4-dithiohydantoin m.p.=87°–8° C.

$C_{19}H_{36}N_2S_2$ requires: C, 63.99%; H, 10.16%; N, 7.56%; S, 17.98%; found: C, 64.12%; H, 10.38%; N, 7.28%; S, 17.86%

EXAMPLE 61

5-Methyl-5-n-undecyl-2,4-dithiohydantoin m.p.=83°–4° C.

$C_{15}H_{28}N_2S_2$ requires: C, 59.95%; H, 9.39%; N, 9.32%; S, 21.34%; found: C, 59.90%; H, 9.48%; N, 9.06%; S, 21.04%

EXAMPLE 62

5-Methyl-5-n-hexyl-2,4-dithiohydantoin m.p.=98°–9° C.

$C_{10}H_{18}N_2S_2$ requires: C, 52.13%; H, 7.88%; N, 12.16%; S, 27.83%; found: C, 52.44%; H, 7.71%; N, 11.88%; S, 27.88%

EXAMPLES 63 TO 65

In order to evaluate the corrosion inhibiting performance of the lubricant compositions of this invention as well as related compositions, a bearing corrosion rig described by Staudt et al (SAE 680538) was used to evaluate the bearing weight loss and colour of Petter W.1. bearings.

This test is run in a 500 Solvent Nuetral oil containing 1% w/w of Lubrizol 1395 and 5% w/w of Lubrizol 894 as a dispersant.

In the test, an acceptable bearing weight loss is one equal to, or less than 16 mg. In the results shown in the colour column of the following Table I, a uniform subjective colour scale is applied, wherein 0=a clear bearing and 3 designates a black bearing.

It should be noted that neither the colour nor the bearing weight loss should be considered in isolation, rather in combination.

TABLE I

| Ex. | Additive | Concentration % w/w | Bearing weight loss (m.g.) | Colour |
|---|---|---|---|---|
| — | None | — | 5.0 | 3 |
| — | A commercially available 2,5-Bis(Alkyldithio)-1,3,4-thiadiazole | 0.5 | 2.0 | 1+ → 2 |
|  |  | 0.2 | 4.6 | 2 |
|  |  | 0.1 | 12.2 | 2+ |
| 63 | Product of Example 2 | 0.5 | 1 |  |
| 64 | Product of Example 3 | 0.2 | 10.9 | 0 |
|  |  | 0.05 | 1.2 | 0 |
| 65 | Product of Example 4 | 0.2 | 11.7 | 1 |
| 66 | Product of Example 5 | 0.5 | 9.8 | 1 |
| 67 | Product of Example 7 | 0.5 | 2.8 | 1 |
| 68 | Product of Example 8 | 0.5 | 14.1 | 1 |
| 69 | Product of Example 9 | 0.1 | 8.5 | 1 |
| 70 | Product of Example 12 | 0.2 | 9.7 | 1 → 1+ |
| 71 | Product of Example 13 | 0.1 | 6.9 | 0 → 1 |
| 72 | Product of Example 15 | 0.1 | 6.8 | 2 |
| 73 | Product of Example 18 | 0.1 | 7.9 | 0 |
| 74 | Product of Example 27 | 0.1 | 10.5 | 1+ |
| 75 | Product of Example 30 | 0.1 | 4.4 | 0 |
| 76 | Product of Example 31 | 0.1 | 0.7 | 1 |
| 77 | Product of Example 32 | 0.1 | 10.8 | 1 → 2 |
| 78 | Product of Example 33 | 0.1 | 6.8 | 1 |
| 79 | Product of Example 34 | 0.1 | 1.0 | 0 → 1 |
| 80 | Product of Example 46 | 0.1 | 10.3 | 0 → 1 |
| 81 | Product of Example 50 | 0.1 | 3.9 | 0 → 1 |
| 82 | Product of Example 51 | 0.1 | 5.3 | 0 |
| 83 | Product of Example 52 | 0.1 | 13.8 | 0 |
| 84 | Product of Example 59 | 0.1 | 6.0 | 2 |
| 85 | 3-(dimethoxyphosphenylethyl)-5,5-dimethyl hydantoin | 0.1 | 10.0 | 0 → 1 |

The above results demonstrate the effectiveness of the compounds of the present invention relative to known corrosion inhibitors.

EXAMPLE 86

3.20 Parts of 5-benzyl-5-n-butyl-2,4-dithiohydantoin, 2.77 parts of di-2-ethylhexylamine and 0.35 parts of paraformaldehyde were refluxed in 100 parts of cyclohexane for 12 hours, the water of reaction being collected in a Dean and Stark water separator. The solution was then cooled and the cyclohexane solvent removed under reduced pressure at 60° C. The residue was filtered through Hyflo (a commercially available filter aid) to give 5.70 parts of 3-(di-2-ethylhexylaminomethyl)-5-benzyl-5-n-butyl-2,4-dithiohydantoin as a pale yellow oil having the following elemental analysis:

$C_{31}H_{53}N_3S_2$ requires: C, 70.00%; H, 10.04%; N, 7.90%; S, 12.05%; found: C, 67.40%; H, 10.42%; N, 7.33%; S, 11.03%

Using the above procedure the following compounds described in Examples 87 to 94 were prepared.

EXAMPLE 87

3-(Pyrrolidinomethyl)-5,5-dibenzylhydantoin $C_{22}H_{25}N_3O_2$ requires: C, 72.70%; H, 6.93%; N, 11.56%; found: C, 72.89%; H, 6.93%; N, 11.53%

EXAMPLE 88

3-(Di-2-ethylhexylaminomethyl)-5,5-2',2',4'-trimethyl cyclopentamethylene-2,4-dithiohydantoin.

$C_{28}H_{53}N_3S_2$ requires: C, 67.86%; H, 10.72%; N, 8.48%; S, 12.94%; found: C, 68.09%; H, 10.77%; N, 8.45%; S, 12.55%

EXAMPLE 89

1,3-Bis(di-2-ethylhexylaminomethyl)-5-methyl-5-isobutyl-2,4-dithiohydantoin.

$C_{42}H_{84}N_4S_2$ requires: C, 71.12%; H, 11.94%; N, 7.90%; S, 9.04%; found: C, 71.04%; H, 11.84%; N, 8.31%; S, 8.82%

EXAMPLE 90

3-(Di-n-octylaminomethyl)-5,5-2'-adamantyl-2,4-dithiohydantoin.

$C_{29}H_{51}N_3S_2$ requires: C, 68.85%; H, 10.16%; N, 8.31%; S, 12.68%; found: C, 69.10%; H, 10.25%; N, 8.14%; S, 12.67%

EXAMPLE 91

1,3-Bis(N'-methylpiperazinomethyl)-5-methyl-5-undecyl-2,4-dithiohydantoin.

$C_{26}H_{52}N_6S_2$ requires: C, 60.89%; H, 10.22%; N, 16.39%; S, 12.50%; found: C, 60.75%; H, 10.49%; N, 16.07%; S, 12.20%

EXAMPLE 92

3-(Di-2-ethylhexylaminomethyl)-5-methyl-5-1'-naphthylhydantoin $C_{31}H_{47}N_3O_2$ requires: C, 75.41%; H, 9.56%; N, 8.51%; found: C, 76.01%; H, 10.27%; N, 7.99%

EXAMPLE 93

3-(Morpholinomethyl)-5,5-cyclopentamethylene-2,4-dithiohydantoin.

$C_{13}H_{21}N_3OS_2$ requires: C, 52.14%; H, 7.07%; N, 14.04%; S, 21.41%; found: C, 52.11%; H, 7.14%; N, 14.01%; S, 21.56%

EXAMPLE 94

3-(Di-2-ethylhexylaminoethyl)-5,5-cyclopentamethylene-2-thiohydantion $C_{25}H_{47}N_3OS$ requires: C, 68.59%; H, 10.82%; N, 9.60%; S, 7.32%; found: C, 68.68%; H, 11.21%; N, 9.12%; S, 7.55%

EXAMPLE 95

A solution of 55.50 parts of methyl cyclohexanone (a commercially available mixture of monomethylated cyclohexanones), 33.80 parts of potassium cyanide, 27.50 parts of ammonium chloride and 38.0 parts of carbon disulphide in 150 parts of aqueous methyl alcohol was gently refluxed at 55° C. to 60° C. for 20 hours. The reaction mass was then steam distilled and the residue allowed to cool. The solid, which crystallised from the solution was filtered and recrystallised from aqueous ethyl alcohol to yield 5,5-methylcyclopentamethylene-2,4-dithiohydantoin having a melting point of 206° C. to 214° C. and the following elemental analysis:

$C_9H_{14}N_2S_2$ requires: C, 50.42%; H, 6.58%; N, 13.07%; S, 29.91%; found: C, 50.16%; H, 6.56%; N, 13.29%; S, 30.55%

Using the above procedure the compound described in Example 96 was prepared.

EXAMPLE 96

5-n-Amyl-5-ethyl-2,4-dithiohydantoin m.p. = 104°-5° C.

$C_{10}H_{18}N_2S_2$ requires: C, 52.13%; H, 7.87%; N, 12.16%; S, 27.83%; found: C, 52.00%; H, 7.99%; N, 12.09%; S, 28.27%

The corrosion inhibiting performance of the above Examples 86–96 have been evaluated in an analogous manner to those listed in Table I (page 51). The further results are listed in Table II.

Table II

| Ex. | Additive | Concentration % w/w | Bearing weight loss (m.g.) | Colour |
|---|---|---|---|---|
| — | None | — | 5.0 | 3 |
| — | A commercially available 2,5-Bis-(alkylthio) 1,3,4-thiadiazole | 0.5 | 2.0 | 1+ → 2 |
|   |   | 0.2 | 4.6 | 2 |
|   |   | 0.1 | 12.2 | 2+ |
| 97 | Product of Example 86 | 0.1 | 2.7 | 0 → 1 |
| 98 | Product of Example 87 | 0.1 | 1.5 | 1 |
| 99 | Product of Example 88 | 0.1 | 2.2 | 1+ |
| 100 | Product of Example 89 | 0.1 | 3.4 | 1 → 1+ |
| 101 | Product of Example 90 | 0.1 | 5.0 | 2 |
| 102 | Product of Example 92 | 0.1 | 3.0 | 0 → 1 |
| 103 | Product of Example 93 | 0.1 | 3.2 | 0 |
| 104 | Product of Example 94 | 0.1 | 2.9 | 0 |
| 105 | Product of Example 96 | 0.1 | 1.7 | 0 |

What is claimed is:

1. A compound of the formula IA

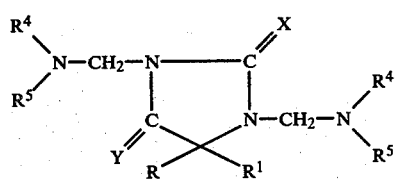

wherein X and Y are the same or different and each is an oxygen or sulphur atom; R and $R^1$ are the same of different and each is hydrogen, a straight or branched chain alkyl group having from 1 to 18 carbon atoms, an alkenyl or alkynyl group having from 3 to 18 carbon atoms, cycloalkyl having from 3 to 12 carbon atoms; said cycloalkyl substituted by methyl; aryl having from 6 to 10 carbon atoms, said aryl substituted by alkyl of 1 to 4 carbon atoms, by one or two chloro groups or by alkoxy of 1 to 4 carbon atoms; aralkyl having from 6 to 10 ring carbon atoms, said aralkyl substituted by methyl, by methoxy or by one or two chloro groups; a heterocyclic residue containing from 3 to 10 ring members or R and $R^1$ together with the carbon atoms to which they are attached form a mono, di-or poly-cyclic ring having from 4 to 12 carbon atoms, these rings may be saturated or unsaturated, they may also be interrupted by heteroatoms; $R^4$ and $R^5$ are the same or different and each is a straight or branched alkyl group having from 1 to 18 carbon atoms, an alkenyl group having from 3 to 8 carbon atoms, a cycloalkyl group having from 3 to 6 ring carbon atoms or benzyl.

2. A compound according to claim 1 wherein at least one of X and Y is sulfur.

3. A compound according to claim 1 wherein both of X and Y are sulfur.

4. A compound according to claim 1 wherein R and $R^1$ are straight- or branched-chain alkyl groups containing from 1 to 8 carbon atoms, or R and $R^1$, together with the carbon atom to which they are attached, form a saturated carbocyclic ring containing from 5 to 12 carbon atoms.

5. A compound according to claim 1 wherein $R^4$ and $R^5$ are straight- or branched-chain alkyl groups containing from 3 to 12 carbon atoms.

6. A compound according to claim 1 wherein X and Y are the same or different and each is oxygen or sulfur, R and $R^1$ are the same or different and each is hydrogen, alkyl of 1 to 9 carbon atoms, cyclopropyl, 4-methyl-3-pentenyl or R and $R^1$ together are tetramethylene or pentamethylene, and $R^4$ and $R^5$ are the same or different and each is alkyl of 1 to 18 carbon atoms, cyclohexyl or benzyl.

* * * * *